(12) United States Patent
De Mathelin et al.

(10) Patent No.: US 10,660,719 B2
(45) Date of Patent: May 26, 2020

(54) MASTER INTERFACE DEVICE FOR A MOTORISED ENDOSCOPIC SYSTEM AND INSTALLATION COMPRISING SUCH A DEVICE

(71) Applicants: UNIVERSITE DE STRASBOURG (ETABLISSEMENT PUBLIC NATIONAL À CARACTÈRE SCIENTIFIQUE, CULTUREL ET PROFESSIONNEL), Strasbourg (FR); CENTRE NATIONAL DE LA RECHERCHE SCIENTIFIQUE (ETABLISSEMENT PUBLIC NATIONAL À CARACTÈRE SCIENTIFIQUE ET TECHNOLOGIQUE), Paris (FR); INSTITUT DE RECHERCHE SUR LES CANCERS DE L'APPAREIL DIGESTIF-IR-CAD (ASSOCIATION RÉGIE PAR LES ARTICLES 21 À 79 DU CODE CIVIL ET LOCAL ET INSCRITE AU REGISTRE DES ASSOCIATIONS DU TRIBUNAL D'INSTANCE DE STRASBOURG), Strasbourg (FR)

(72) Inventors: Michel De Mathelin, Strasbourg (FR); Florent Le Bastard, Ribeauville (FR); Florent Nageotte, Wettolsheim (FR); Philippe Zanne, Roppenheim (FR); Lucile Zorn, Colmar (FR)

(73) Assignees: Universite De Strasbourg, Strasbourg (FR); Centre National De La Recherche Scientifique, Paris (FR); Institut De Recherche Sur Les Cancers De L'Appare-, Strasbourg (FR)

( * ) Notice: Subject to any disclaimer, the term of this patent is extended or adjusted under 35 U.S.C. 154(b) by 277 days.

(21) Appl. No.: 15/113,820

(22) PCT Filed: Jan. 22, 2015

(86) PCT No.: PCT/EP2015/051189
§ 371 (c)(1),
(2) Date: Jul. 23, 2016

(87) PCT Pub. No.: WO2015/110495
PCT Pub. Date: Jul. 30, 2015

(65) Prior Publication Data
US 2016/0338789 A1     Nov. 24, 2016

(30) Foreign Application Priority Data
Jan. 23, 2014    (FR) ...................................... 14 50560

(51) Int. Cl.
*A61B 34/00* (2016.01)
*G05G 9/047* (2006.01)
(Continued)

(52) U.S. Cl.
CPC .............. *A61B 34/74* (2016.02); *A61B 34/25* (2016.02); *A61B 34/30* (2016.02); *A61B 34/35* (2016.02);
(Continued)

(58) Field of Classification Search
CPC ........... A61B 1/00133; A61B 1/00149; A61B 1/0016; A61B 34/74; A61B 34/25;
(Continued)

(56) References Cited

U.S. PATENT DOCUMENTS

| | | | |
|---|---|---|---|
| 2003/0109957 A1* | 6/2003 | Sanchez | ................ A61B 34/30 700/245 |
| 2009/0192519 A1* | 7/2009 | Omori | ................ A61B 19/2203 606/130 |

(Continued)

FOREIGN PATENT DOCUMENTS

| | | |
|---|---|---|
| DE | 2504663 A1 | 8/1976 |
| DE | 3928532 A1 | 3/1991 |

(Continued)

OTHER PUBLICATIONS

A. De Donno, et al., "Introducing STRAS: A New Flexible Robotic System for Minimally Invasive Surgery"; IEEE International Conference on Robotics and Automation (ICRA 2013), Karlsruhe, Germany, May 2013.

(Continued)

*Primary Examiner* — Ryan N Henderson
*Assistant Examiner* — Pamela F Wu
(74) *Attorney, Agent, or Firm* — Whitmyer IP Group LLC

(57) ABSTRACT

A master interface device for remotely controlling at least one instrument mounted in an endoscope. The device includes at least one control handle device in the form of a subassembly able to be manipulated in the same degrees of freedom as the associated control instrument. The control device includes on the one hand a gripping and manoeuvring shaft, designed for gripping with the whole hand by the operator, and on the other hand a mounting bracket supporting said shaft. Translation and pivoting of the bracket controls respectively translation and rotation around itself of the associated instrument, and the pivoting of the shaft relative to the bracket controls the bending of the end of the instrument concerned.

18 Claims, 14 Drawing Sheets

(51) Int. Cl.
  *A61B 34/30* (2016.01)
  *A61B 34/37* (2016.01)
  *A61B 34/35* (2016.01)
(52) U.S. Cl.
  CPC .............. *A61B 34/37* (2016.02); *G05G 9/047* (2013.01); *A61B 2034/301* (2016.02); *A61B 2034/742* (2016.02); *G05G 2009/04714* (2013.01)
(58) Field of Classification Search
  CPC ......... A61B 34/30; A61B 34/35; A61B 34/37; A61B 2034/742; A61B 34/76; A61B 34/77; A61B 2034/302–305; A61B 2034/301–306; A61B 34/32; A61B 34/70–74; A61B 2034/715; A61B 2034/741–744; A61B 34/75–77; G05G 9/047; G05G 2009/04703; G05G 2009/04707; G05G 2009/04711; G05G 2009/04714; G05G 2009/04718; G05G 2009/04722; G05G 2009/04725; G05G 2009/04729; G05G 2009/04733; G05G 9/04737; G05G 2009/0474; G05G 2009/04744; G05G 2009/04748; G05G 2009/04751; G05G 2009/04755; G05G 2009/04759; G05G 2009/04762; G05G 2009/04766; G05G 2009/0477; G05G 2009/04774; G05G 2009/04777; G05G 2009/04781; G05G 9/04785; G05G 9/04788
  USPC ........ 600/106–107, 102, 114, 118, 139–142, 600/146
  See application file for complete search history.

(56) References Cited

U.S. PATENT DOCUMENTS

| | | | |
|---|---|---|---|
| 2011/0022229 A1* | 1/2011 | Jang | B25J 3/04 700/248 |
| 2012/0221145 A1* | 8/2012 | Ogawa | B25J 3/04 700/259 |
| 2014/0046128 A1* | 2/2014 | Lee | A61B 1/00009 600/102 |
| 2014/0276646 A1* | 9/2014 | Wong | A61M 25/0105 604/528 |
| 2014/0378995 A1* | 12/2014 | Kumar | A61B 19/2203 606/130 |
| 2015/0090065 A1* | 4/2015 | Kishi | B25J 13/02 74/491 |

FOREIGN PATENT DOCUMENTS

| | | |
|---|---|---|
| DE | 4213418 A1 | 10/1992 |
| DE | 19918961 A1 | 11/2000 |
| EP | 0078017 A2 | 5/1983 |
| EP | 1726254 A1 | 11/2006 |
| WO | 2013132194 A1 | 9/2013 |

OTHER PUBLICATIONS

Antonio De Donno, et al., "Master/Slave Control of Flexible Instruments for Minimally Invasive Surgery"; IEEE/RSJ International Conference on Intelligent Robots and Systems (IROS 2013), Nov. 3-7, 2013. Tokyo, Japan.
B. Bardou et al., "Control of a multiple sections flexible endoscopic system"; International Conference on Intelligent Robots and Systems (IROS), Taipei, Taiwan, pp. 2345-2350, Oct. 2010.
B. Bardou et al., "Design of a robotized flexible endoscope for natural orifice transluminal endoscopic surgery"; Computational Surgery and Dual Training, M. Garbey et al (Eds.), chapter 9, pp. 155-170, Springer, ISBN: 978-1-4419-1122-3, 2010.
B. Bardou et al., "Design of a Telemanipulated System for Transluminal Surgery"; IEEE Engineering in Medicine and Biology Conference (EMBC 2009), Minneapolis, MN, United States, Sep. 2009.

* cited by examiner

MASTER INTERFACE DEVICE FOR A MOTORISED ENDOSCOPIC SYSTEM AND INSTALLATION COMPRISING SUCH A DEVICE

TECHNICAL FIELD

The present invention relates to the field of remotely controlling instruments in several degrees of freedom, in particular instruments forming part of a robotised or motorised endoscope system, and its subject matter is a master control interface device and an endoscopic medical installation comprising such a device.

BACKGROUND

Numerous designs of medical endoscopic devices are already known, for example from documents DE 3928532, DE 19918961, EP 1 726 254 and DE 2504663.

In order to limit the effort required by the operator and make the use of the endoscope and it instruments easier, simpler and safer, particularly during precise interventions that take a long time, it has been proposed to motorise at least some of the manoeuvres and actions, in particular those associated with the bending of the ends of instruments and the operation of tools.

Earlier motorised designs of this kind are known in particular from documents DE 2504663, EP 0 078 017, DE 4213418, as well as from the following publications:

"Design of a Telemanipulated System for Transluminal Surgery", B. Bardou et al.: IEEE Engineering in Medicine and Biology Conference (EMBC 2009), Minneapolis, Minn., United States, September 2009;

"Control of a multiple sections flexible endoscopic system", B. Bardou et al.: International Conference on Intelligent Robots and Systems (IROS), Taipei, Taiwan, pp. 2345-2350, October 2010;

"Design of a robotized flexible endoscope for natural orifice transluminal endoscopic surgery", B. Bardou et al.: Computational Surgery and Dual Training", M. Garbey et al (Eds.), chapter 9, pp. 155-170, Springer, ISBN: 978-1-4419-1122-3, 2010.

An additional step in the motorisation and increase of comfort and effective use of such endoscopes has been achieved by the embodiment described in document WO-A-2013/132194, as well as in document: "Introducing STRAS: A New Flexible Robotic System for Minimally Invasive Surgery"; A. De Donno, L. Zorn, P. Zanne, F. Nageotte, M. de Mathelin; IEEE International Conference on Robotics and Automation (ICRA 2013), Karlsruhe, Germany, May 2013.

However, despite the assistance provided by this generalised motorisation of the endoscope and its instruments, the aforementioned known systems do not meet the expectations of operators (generally surgeons) in an optimal manner, because of the lack of user-friendliness and ergonomics of the currently available handling interfaces which lead to fatigue and stiffness after prolonged use. Said known interfaces usually only provide a limited, or even non-existent, intuitive use, and because of this require a long and tedious training period.

Furthermore, the structures of the existing interfaces are generally relatively complex and fragile.

These disadvantages, as well as the presence of control elements that are often ill-adapted to the control of the instruments, have been verified in particular by the authors of document: "Master/Slave Control of Flexible Instruments for Minimally Invasive Surgery"; Antonio De Donno, Florent Nageotte, Philippe Zanne, Lucile Zorn, Michel De Mathelin; IEEE/RSJ International Conference on Intelligent Robots and Systems (IROS 2013).

Finally, US 2003/0109957 discloses a microwrist system with a master interface device for remotely controlling at least one medical instrument for investigation or surgical intervention, wherein said or each instrument has several motorised degrees of freedom, and among them an ability to perform a translation movement relative to a canula, an ability to rotate around itself and an ability to bend the operational distal end of the instrument supporting the tool or similar effector.

This known master interface device is able to deliver signals for actuating units controlling the three degrees of freedom of the instrument or each instrument concerned and said master interface device comprises two control handle devices and a display screen of a video image of the intervention or investigation site provided by the system.

Each control handle device consists of a sub-assembly able to be manipulated with the same degrees of freedom as the associated controlled instrument and comprising a gripping and manoeuvring handle shaft, designed to be gripped with the whole hand by the operator, and a mounting bracket supporting said shaft.

Each handle shaft is pivotally mounted on the corresponding bracket, its physical axis being identical with its pivoting axis.

Said brackets are themselves pivotally mounted on bar structures extending laterally on both sides along the operator's forearms and chair. Said bar structures are linked to a support structure located behind the operator's back via successive elbow and shoulder joints.

Thus, the system according to US 2003/0109957 is quite cumbersome and complex, extends all around the operator and is not satisfactory in terms of intuitiveness and user comfort.

SUMMARY

In this context, the essential aim of the present invention is to provide a master handling interface of at least one endoscope instrument, the use of which is intuitive, ergonomic and easy and the construction of which is simple and robust.

To this effect, the subject matter of the invention is a master interface device for remotely controlling at least one medical investigation device or surgical intervention device mounted in an endoscope forming part of an endoscopic system, in particular of the flexible type, in which said or each instrument has three motorised degrees of freedom, namely an ability to perform a translational movement relative to the endoscope, an ability to rotate around itself and an ability to bend the distal operational end of the instrument bearing the tool or similar effector, said master interface device being able and designed to supply control signals, position and/or displacement signals to activating units controlling the three degrees of freedom of the instrument or each instrument concerned, said master interface device comprising at least one manual control handle device and a screen for displaying a video image of the intervention or investigation site provided by the endoscopic system, the or each control handle device consisting of a sub-assembly able to be manipulated in the same degrees of freedom as the associated controlled instrument and comprising on the one hand a gripping and manoeuvring shaft, designed to be gripped by the whole hand of the operator and on the other hand a mounting console supporting said shaft, for example in the form of a bracket, said master interface device being characterised in that the shaft is connected to the mounting console by a pivot connection with an axis which is offset from said shaft, and in that said console is connected to a support structure forming a fixed reference point by a connection with the ability to pivot and perform a translation movement according to mutually parallel or combined axes, the axes of the two pivot connections being mutually intersecting, and in that the translation and pivoting of the console control respectively the translation and rotation around itself of the associated instrument and the displacement of the shaft relative to the console, along a circular trajectory centred on the pivot axis, controls the bending of the end of the instrument concerned.

BRIEF DESCRIPTION OF THE DRAWINGS

The invention is described in more detail by way of the following description which relates to a preferred embodiment, given as a non-restrictive example, and explained with reference to the accompanying schematic drawings, in which.

DETAILED DESCRIPTION

Figure 1:
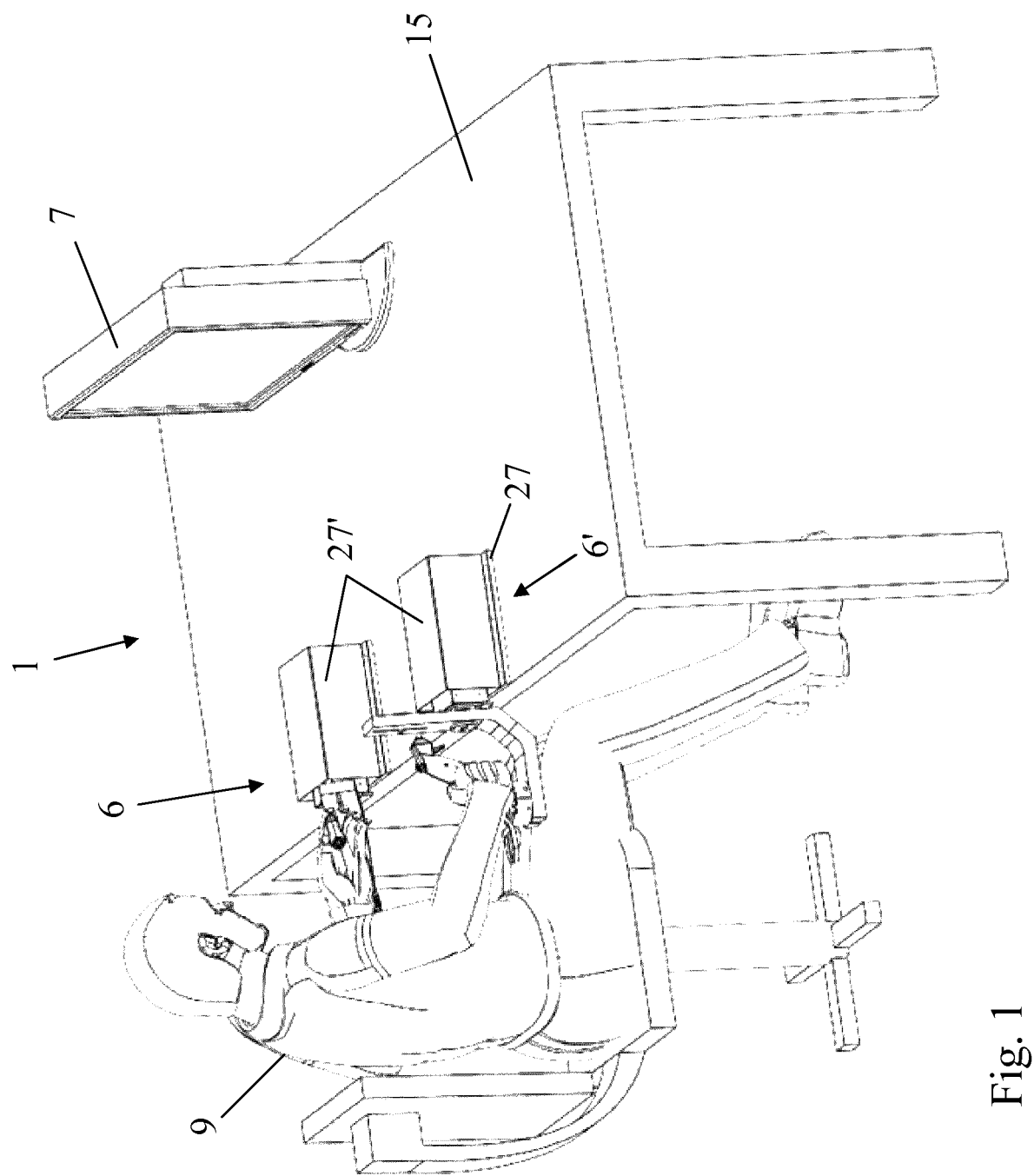
FIG. 1 is a perspective view of a master interface device according to the invention, comprising two control handle devices manipulated by an operator.
Figure 2:
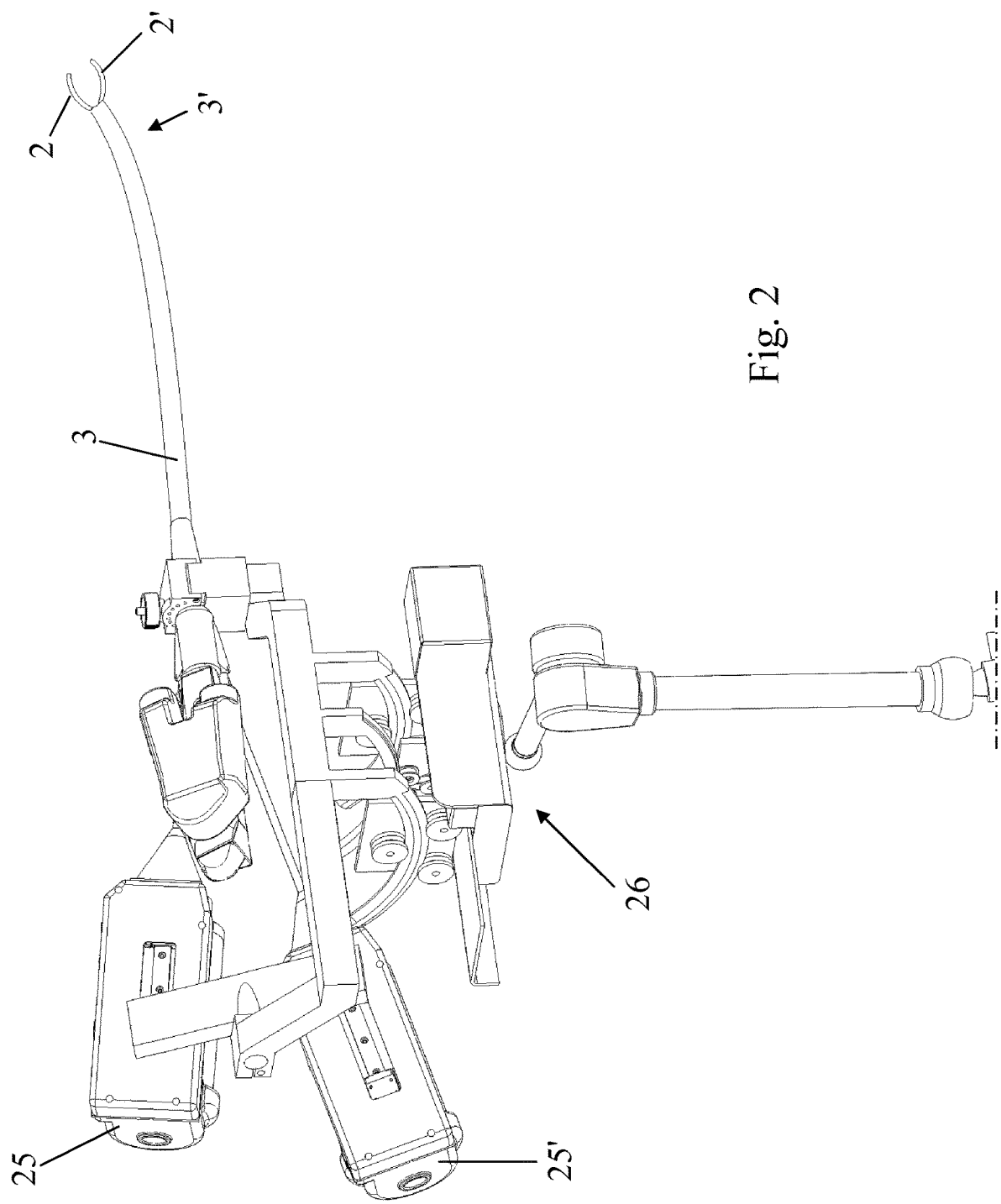
FIG. 2 is a simplified representation of an example of an endoscopic system with a flexible endoscope and two instruments, and which can be controlled, at least as far as the instruments are concerned, by the master interface device represented in FIG. 1 (such an endoscopic system is known for example from document WO-A-2013/132194)
Figure 3:
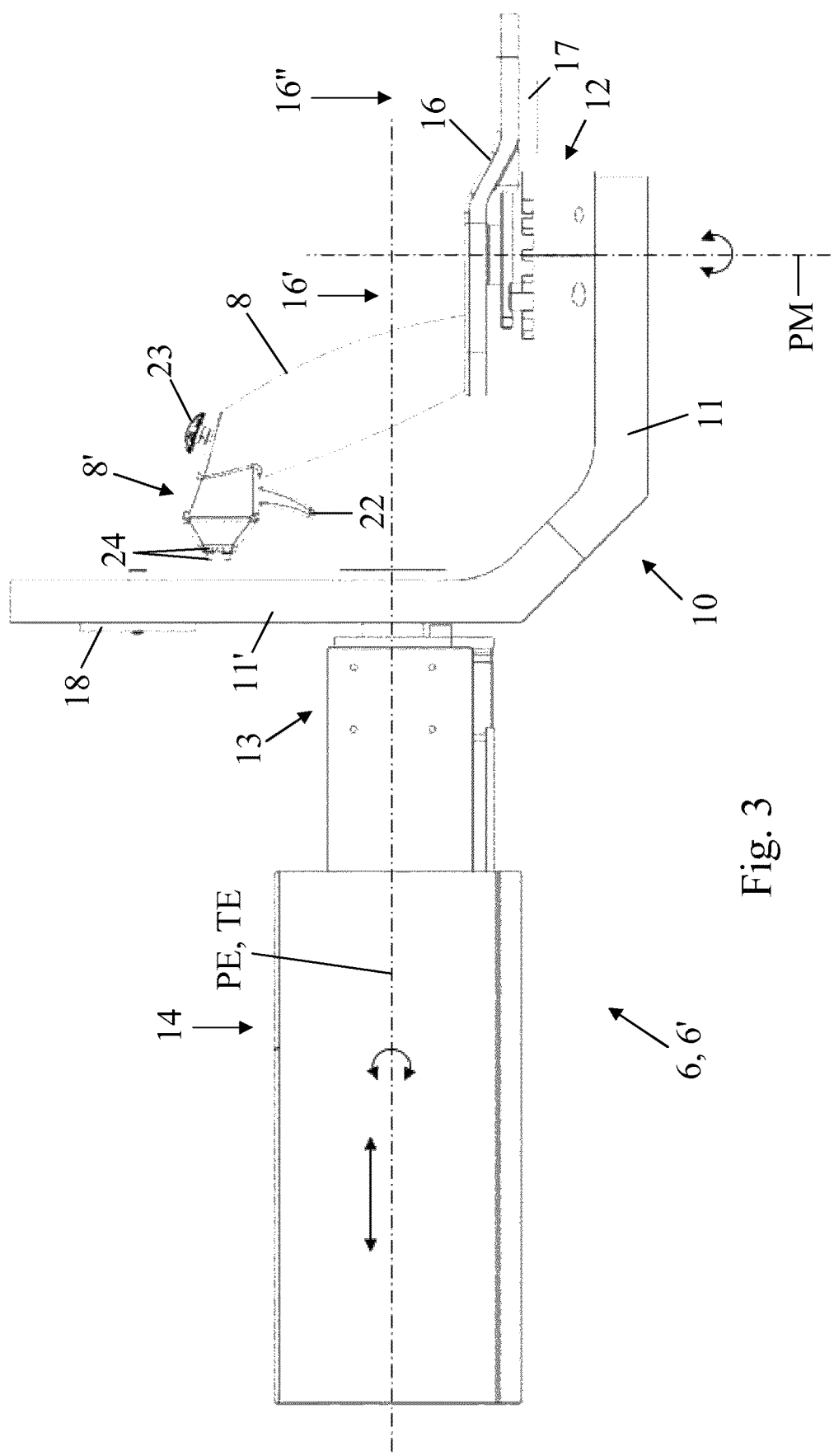
FIG. 3 is a view in lateral elevation and on a different scale of a control handle device forming part of the master interface device shown in FIG. 1, said handle device being in a neutral resting position.
Figure 4A:
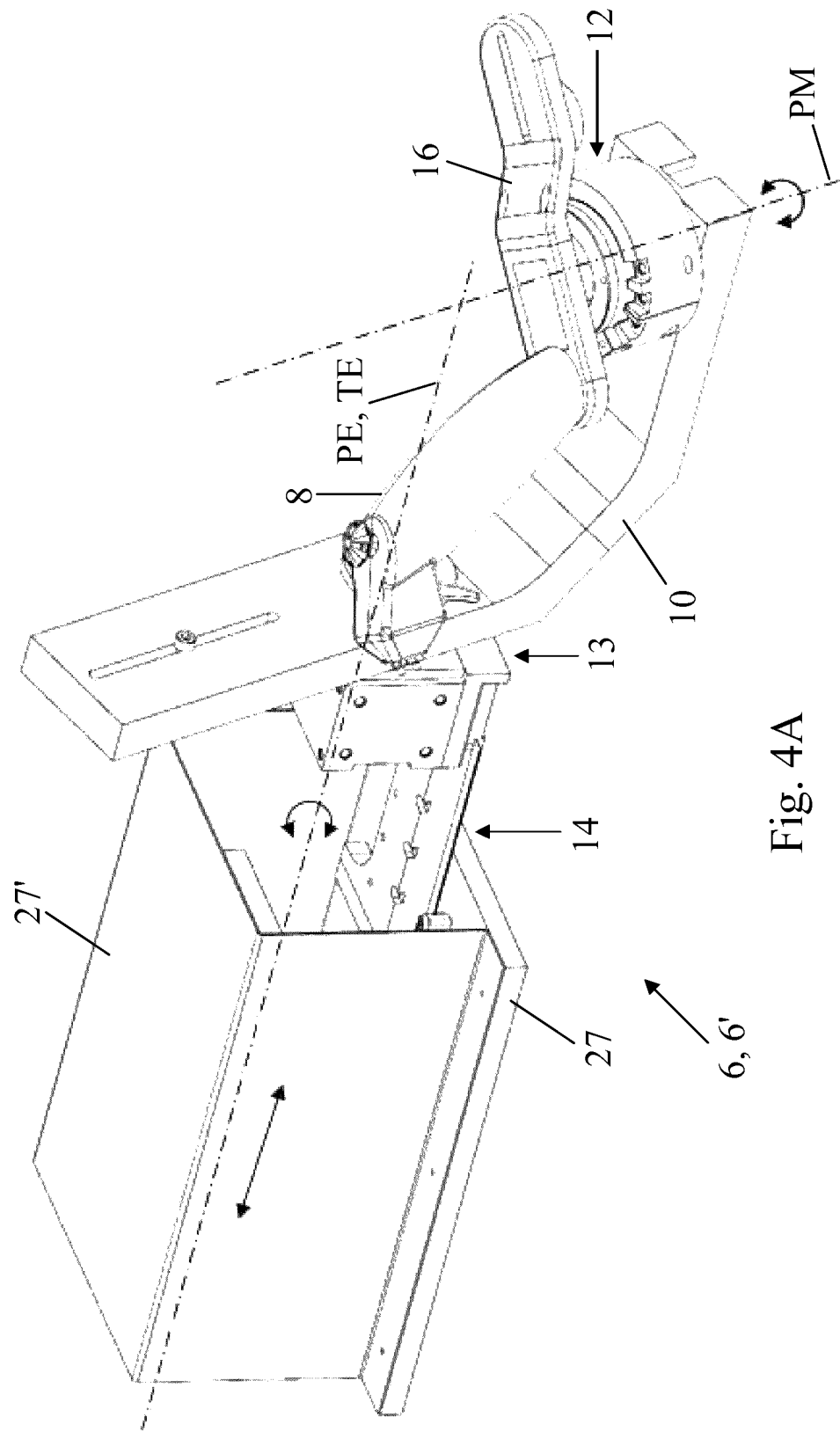
FIGS. 4A and 4B are perspective views in two different directions of the control handle device of FIG. 3, in a configuration obtained after manipulation by an operator (pivoting of the shaft/translation and pivoting of the bracket)

FIG. 1, in relation to FIG. 2, and partly FIGS. 3 and 4 show a master interface device 1 for remotely controlling at least one medical investigation instrument or surgical intervention instrument 2, 2' mounted in an endoscope 3 forming part of an endoscopic system 4, in a flexible, motorised or robotised type system.

Said or each medical instrument 2, 2' has three motorised degrees of freedom, namely the ability TI to move in translation relative to the endoscope 3, an ability RI to rotate around itself and an ability FI to bend the operational distal end 5 of the instrument 2, 2' concerned bearing the tool or similar effector 5'.

Said master interface device 1 is able and designed to provide control signals, position and/or displacement signals to actuating units 25, 25' controlling the aforementioned three degrees of freedom of the instrument or each instrument 2, 2' concerned.

The method of transmitting signals between the master interface device 1 (possibly from the or from each control handle device 6, 6') and the units 25, 25' (or a system for driving the latter) is preferably via a wired connection. However, wireless transmission is also possible.

Furthermore, as a function of the nature of the transmitted signals and the means of treatment provided or not provided by the device 1 and/or units 25, 25', said signals can be transmitted directly between said device 1 and said units 25, 25' or then transmitted by an intermediate electronic/computer means for evaluating the measurement signals and generating control signals (not shown) thus forming a system for driving said units 25, 25'.

Figure 9A:
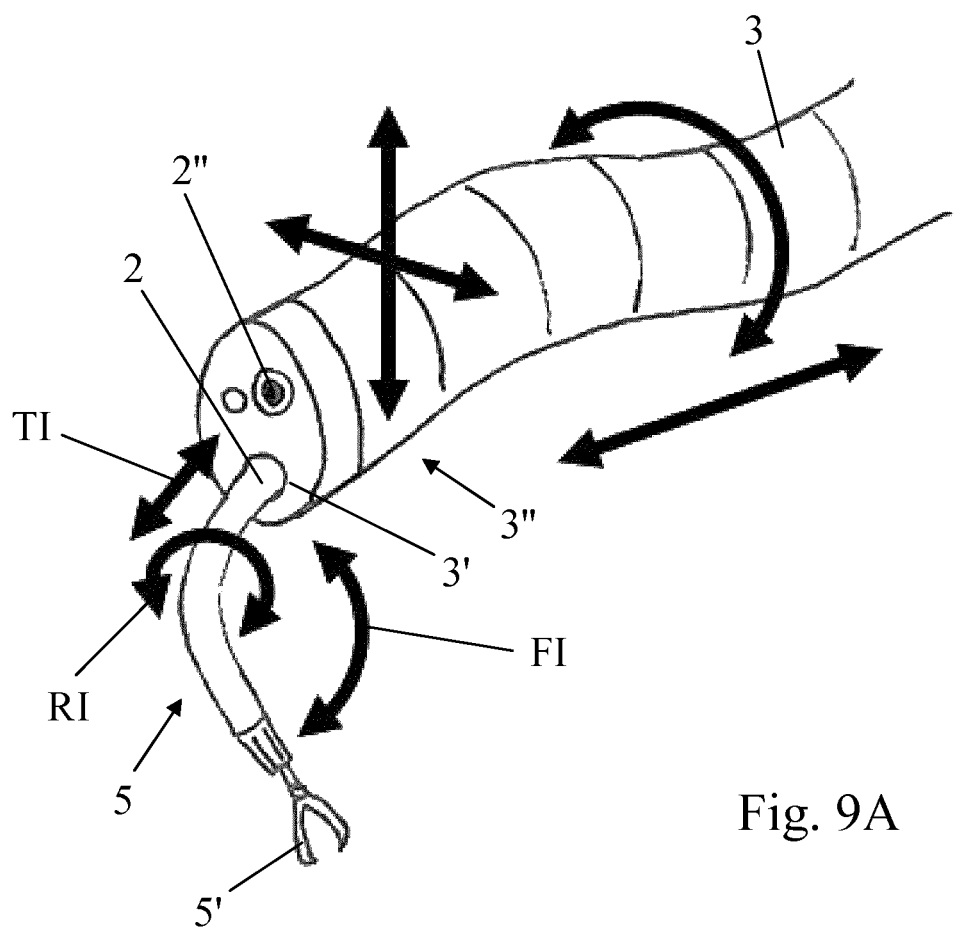
FIGS. 9A and 9B are partial views in perspective of two ends of flexible endoscopes, illustrating the degrees of freedom of the latter and the instrument (FIG. 9A) or instruments (FIG. 9B) accommodated in the working channel or channels.
Figure 9B:
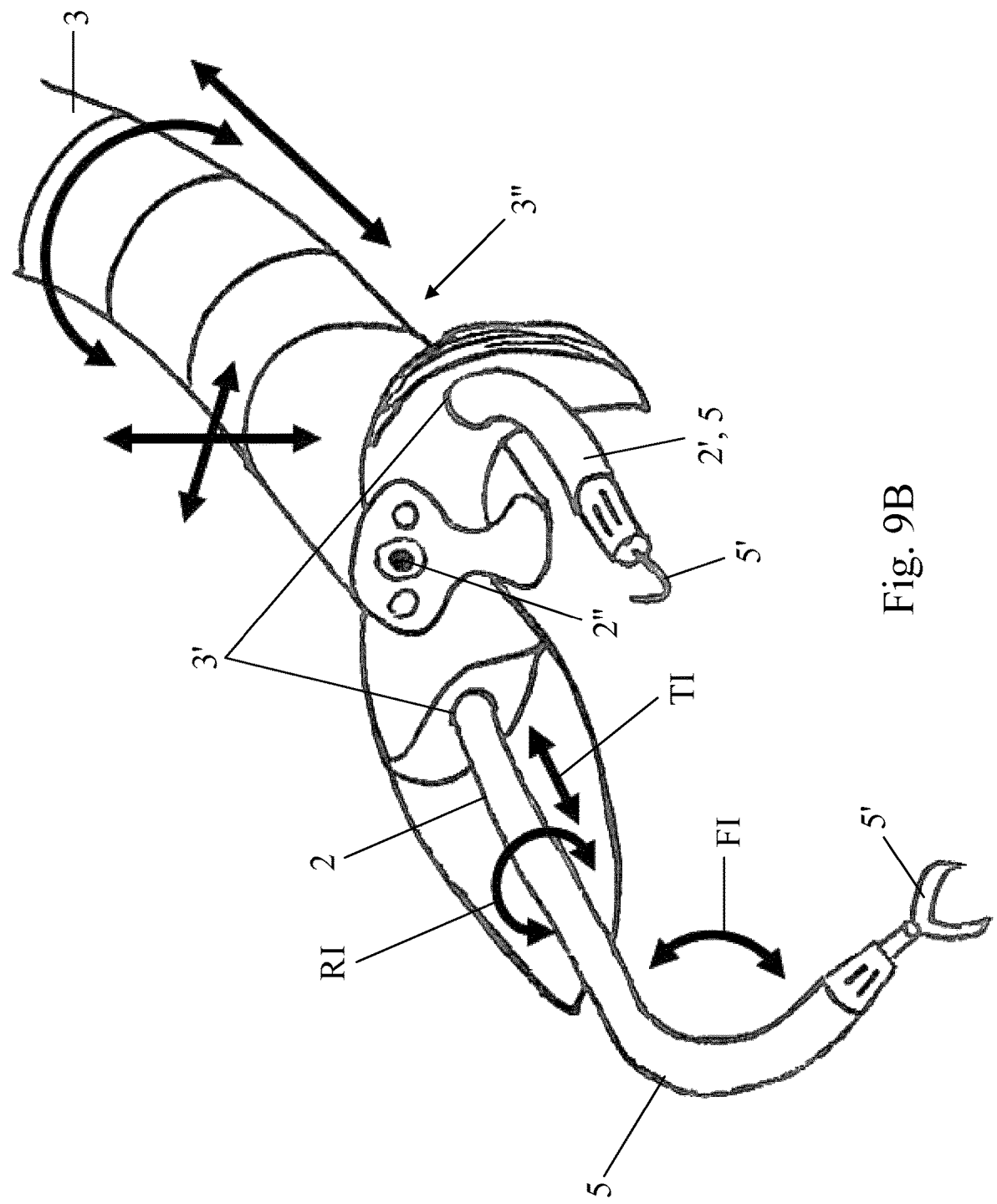

The master interface device 1 also comprises at least one manual control handle device 6, 6' and a screen 7 for displaying a video image of the intervention or investigation site provided by the endoscopic system 4 (for example: a camera 2", the lens of which is arranged at the end 3" of said endoscope and the signal transmission lines of which are arranged in a channel of the endoscope—FIGS. 9A and 9B).

The or each control handle device 6, 6' consists of a subassembly which can be manipulated with the same degrees of freedom as the associated controlled instrument 2, 2' and comprises on the one hand a gripping and manoeuvring shaft 8, designed to be gripped by the whole hand of the operator 9, on the other hand a mounting console or bracket 10 supporting said shaft 8.

According to the invention:

the shaft 8 is connected to the mounting console 10 by a pivot connection 12 with an axis PM which is offset from said shaft 8 and said console 10 is connected to a support structure 15 forming a fixed reference by a connection 13, 14 able to pivot and perform a translation movement according to the axes PE, TE which are mutually parallel or combined, the axes PM and PE of the two pivot connections 12, 13 being mutually intersecting, and the translation and pivoting of the console 10 controls respectively the translation and rotation around itself of the associated instrument 2, 2' and the displacement of the shaft 8 relative to the bracket 10, along a circular trajectory centred on the pivot axis PM, controls the bending of the end 5 of the concerned instrument 2, 2'.

By means of the aforementioned arrangements, the invention provides the operator, at the or each control handle 6, 6', similar degrees of freedom to those at the flexible distal end part 5 of the instrument 2, 2' concerned: thus it is sufficient for the operator 9, by making use of the real time video link or display (images of the intervention site with the ends of the instruments 2, 2' provided by the endoscopic camera 2"), to perform with the handle the movements and manipulations that he wishes to see replicated in said associated instrument 2, 2'. Thus the operator moves his hand or hands as if he were holding the end of an instrument 2, 2' in the latter (in the presence of a single instrument associated with a single control handle) or in each of the latter (in the presence of two instruments 2, 2' each associated with a control handle 6, 6').

Thus, according to the invention, the architecture of each control handle device 6, 6' is specifically designed to be adapted to the architecture of the medical instrument 2, 2' that it controls (see FIGS. 9A and 9B). This architecture gives to the operator (generally a surgeon) the feeling of directly manipulating the tool 5' while moving the gripping and manoeuvring shaft 8 of the handle device 6, 6' and provides him with the position and orientation of the distal operational section 5 of the controlled medical instrument 2, 2'. This advantageous property is in particular obtained thanks to the offset between the shaft 8 and the pivot axis PM of said shaft with respect to the segment 11 of the mounting bracket 10. Thus, the pivot axis PM and the longitudinal median axis MA of said shaft 8 do not coincide, which results constructively in an offset distance d between the pivot connection 12 and the shaft 8. This offset distance d induces a displacement of the shaft 8 along a circular trajectory (and not a rotation around its own longitudinal median axis), the radius of said trajectory corresponding to said offset distance. So the control handle device 6, 6' renders not only the orientation and translatory position, but also the bending of the distal operational section 5 of the controlled medical instrument 2, 2' to the operator, as the tool 5' is also moving along a similar roughly circular trajectory when the distal operational section 5 is bent. This similarity of position, state and movement between the master interface and the slave device, respectively 1 and 2, 2', makes the use of the global endoscopic system 4 really intuitive.

Figure 5:
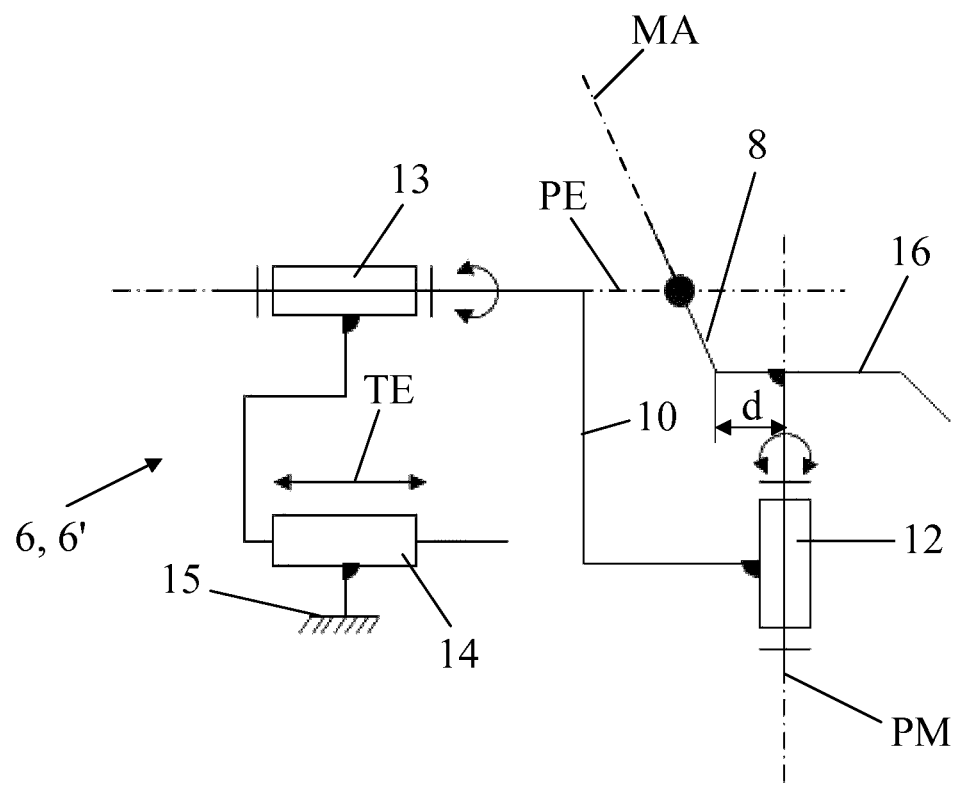
FIG. 5 is an equivalent symbolic representation of the handle device of FIGS. 3 and 4 illustrating the degrees of freedom between the different constituent parts of said device.

Furthermore, as the control handle device kinematics is realized by means of an articulated structure composed of successive rigid segments joined together by connections 12, 13, 14, the result is a simple, inexpensive and robust structure that addresses the problems associated with the control of flexible systems (cf. in particular FIG. 5).

Furthermore, the pivot connections 12 and 13, as well as the translation connection 14, can be provided with mechanical stops which limit the ranges of movements to those that are authorised or possible at the end of the instrument 2, 2' concerned.

The support structure 15 can for example consist of a table or a desk (FIG. 1) dedicated specifically to holding the master interface device 1 (if necessary permanently) or onto which the components 6, 6', 7 of said device 1 are fixed/placed temporarily.

In an advantageous manner and in order to reproduce at the level of the handle device 6, 6', the geometric configuration governing the translation (TI) and the rotation (RI) of the end 5 of the instrument 2, 2' concerned (see FIGS. 9A and 9B), the pivot axes PM and PE of the shaft 8 and of the console 10 are substantially perpendicular to one another (see FIGS. 3 to 5).

Furthermore, in order to reproduce the kinematic singularity of the instrument 2, 2' when in a straight or extended position, the shaft 8 is preferably mounted on the console 10 and the latter on the fixed structure 15 in such a manner that the hand of the operator 9 gripping said shaft 8 is located so as to face (substantially aligned and in front of) the pivot connection 13 between the console 10 and the support structure 15 (see in particular FIGS. 1, 3 and 5).

With an arrangement of the various connections as indicated before, the resulting structure of each control handle device 6, 6' is compact and extends over a limited space only, in front of the hands of the operator.

As shown in FIGS. 1 and 3 to 7, the mobile mounting console 10 consists preferably of a simple bracket or L-shaped element with a first branch 11 supporting the shaft 8 (through the pivot connection 12) and a second branch 11' connected to the fixed support structure 15 (complex connection 13, 14 with two degrees of freedom).

However, other forms are possible for the console 10, whilst maintaining the other arrangements of the invention.

Figure 10:
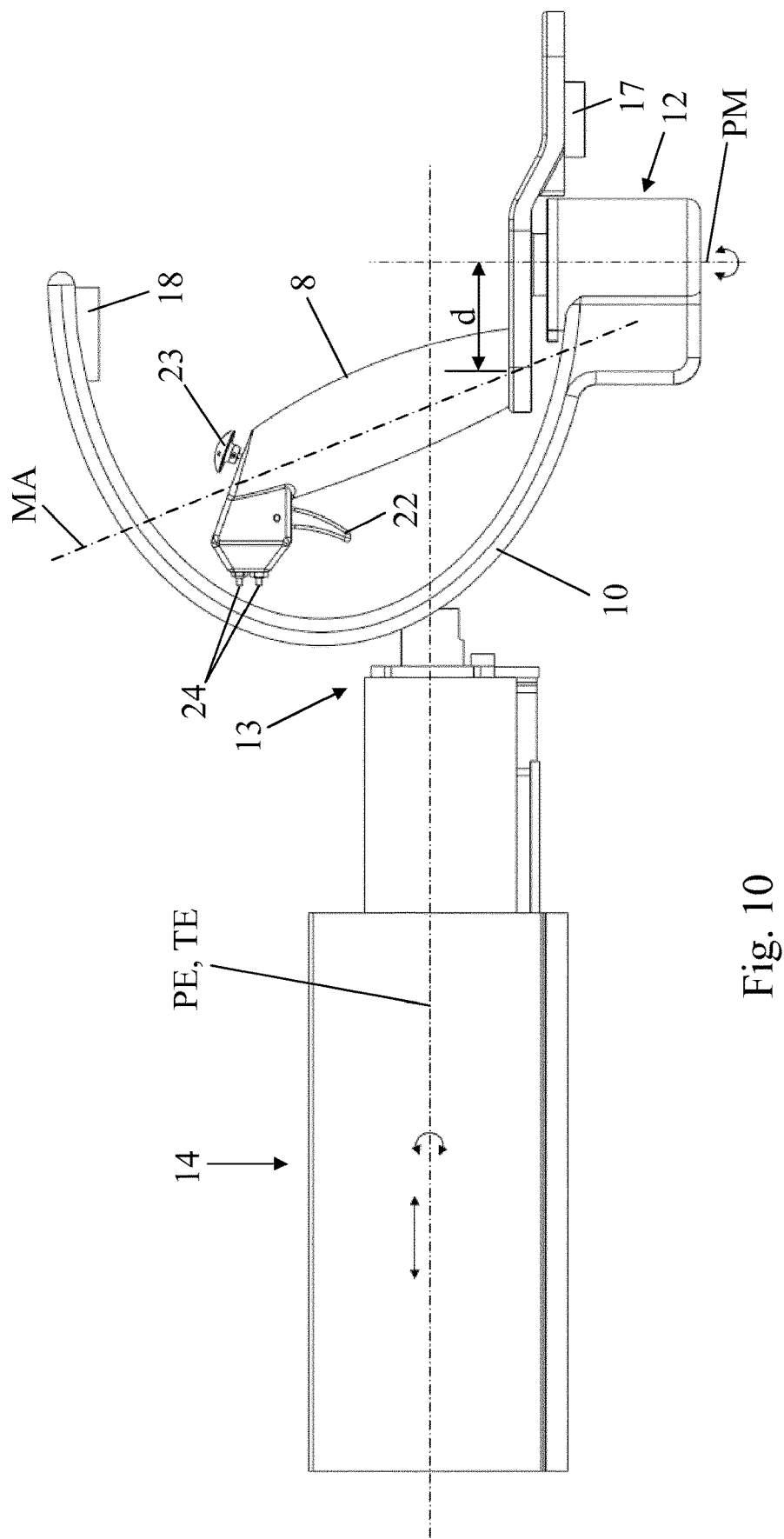
FIG. 10 is a view similar to FIG. 3 of a control handle device with an embodiment of the mounting console in the shape of a C.
Figure 11:
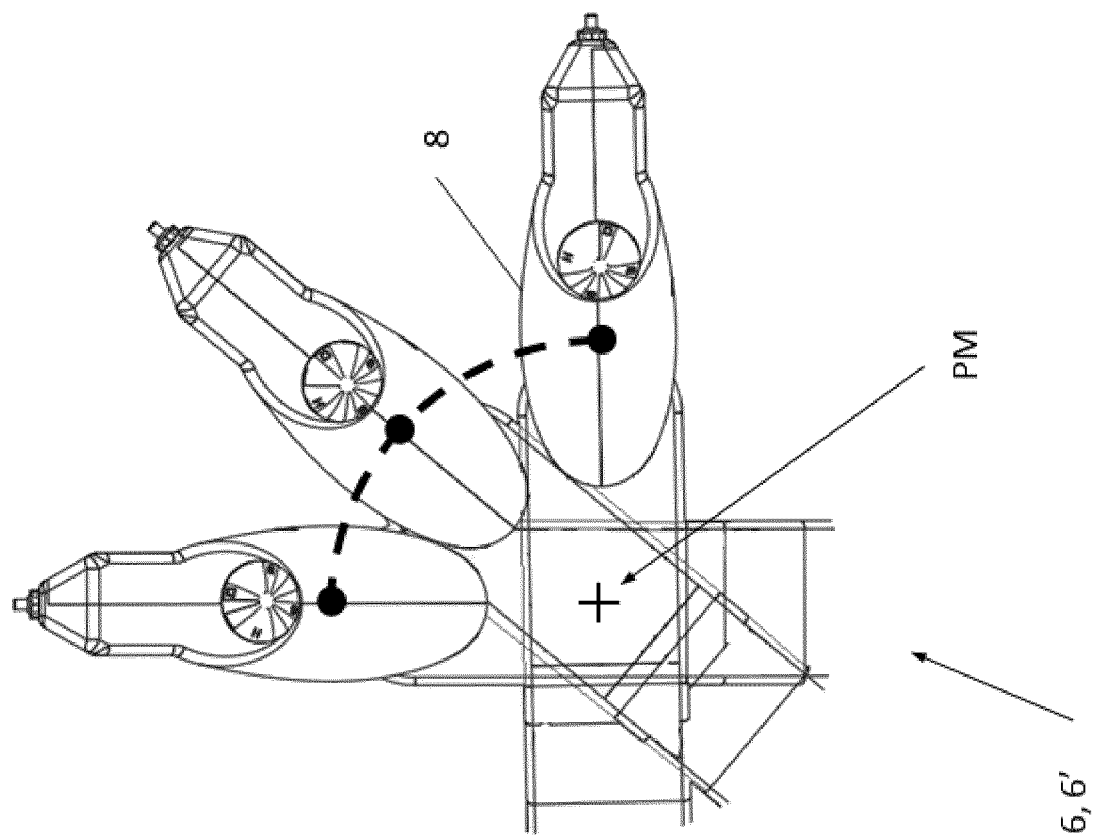
FIG. 11 shows partial top views of both distal end of an endoscope with a medical instrument and control handle device, illustrating the similarity between the bending of the distal end of the instrument and the circular displacement of the gripping and manoeuvring shaft around its pivot axis, and, FIG. 12 shows perspective views of the distal end of an endoscopic instrument (as shown in FIG. 11) and of the corresponding control handle device, illustrating the correspondence between the rotation and bending angles of said distal end and the rotation angles of the components of the control handle device.
Figure 11:
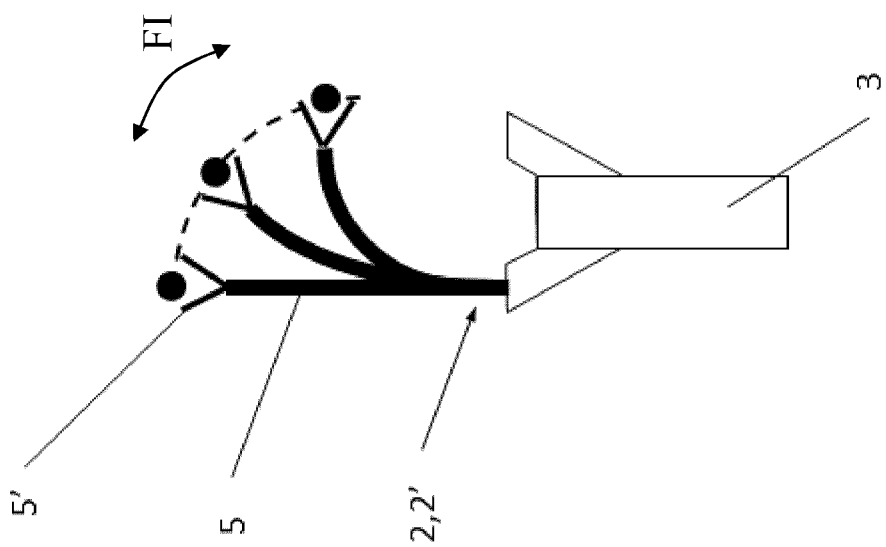
Figure 12:
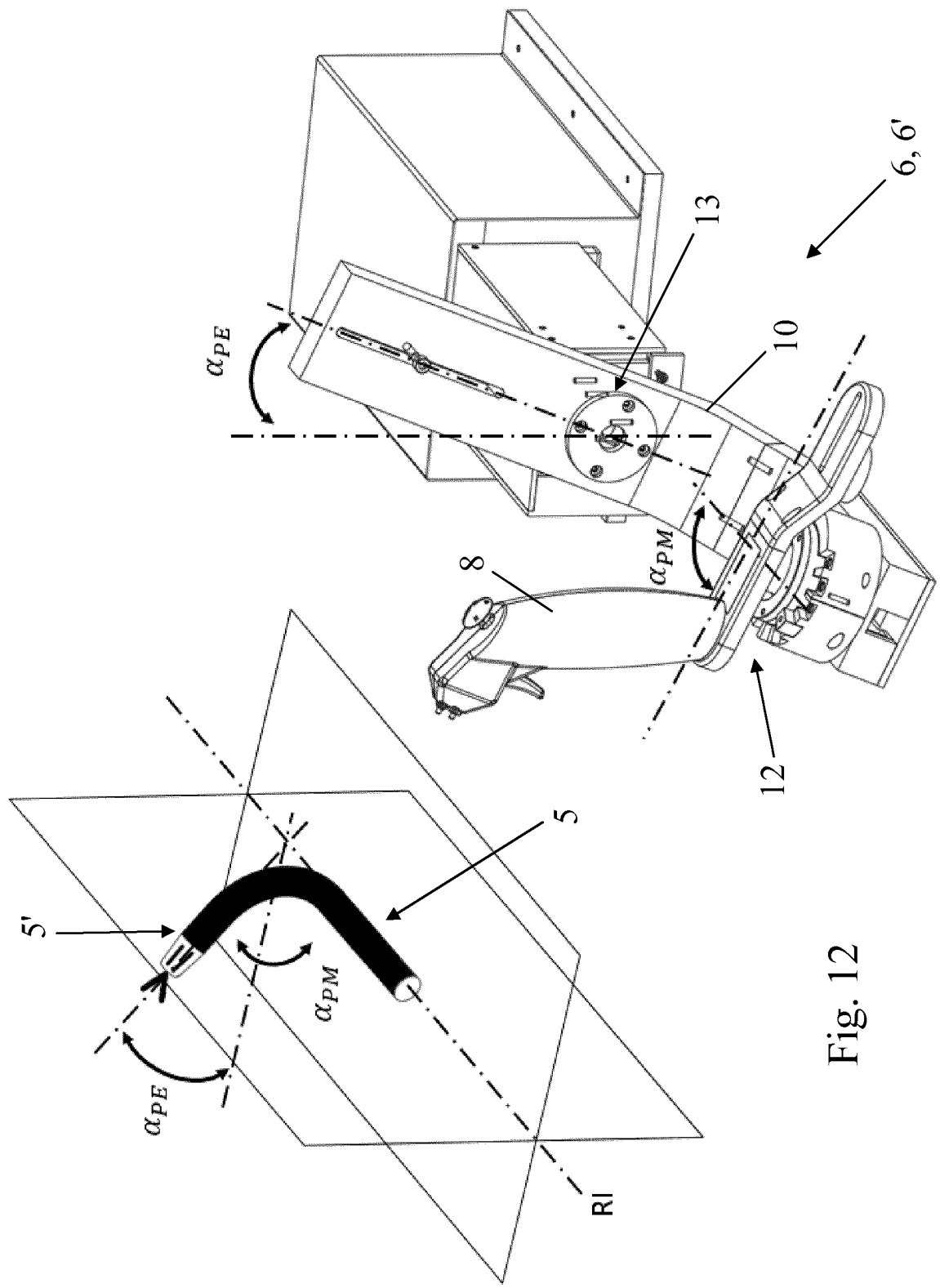

Thus, FIG. 10 shows by way of example a console 10 in the shape of a C.

To be able to practically simulate, in a realistic and simple manner, the bending (FI) of the end 5 of the instrument 2, 2' controlled by the concerned associated handle device 6, 6', it is advantageous, as shown in FIGS. 3 to 8, that the shaft 8 is (rigidly) mounted on a support part 16 with an elongated form connected by the pivot connection 12 to a first branch 11 of the mounting bracket 10. Said support part 16 provides the offset distance d between said connection 12 and said shaft 8 (in the plane perpendicular to the pivot axis PM).

Preferably the structure and arrangement of the shaft 8, support 16 and pivot connection 12 are such that the articulation of the wrist of the operator is substantially located above the pivot connection 12, when he grips the shaft 8.

Thus, said support part 16 ensures a physically guided displacement of said shaft 8 according to a circular trajectory centred on the pivot axis PM of the aforementioned pivot connection 12.

Furthermore, the support part 16 may also provide a bearing surface for the hand, wrist and possibly the forearm of an operator 9 holding said shaft 8 (in particular during a rest phase, when the respective hand is not being used for manoeuvring the associated instrument 2, 2'). This bearing surface for the hand and wrist can be provided by a section 16' of the support part 16 extending between the shaft 8 and the location of pivot connection 12 and the possible bearing surface for the forearm may be provided by an additional section 16" of the support part 16 extending beyond said connection 12, opposite the shaft 8.

Additionally, the shaft 8 is preferably slightly inclined forward so that the axis MA of the shaft 8 forms an angle with the axis PM of the pivot connection 12.

According to an advantageous feature of the invention, which makes it possible to reduce the effort of the operator 9 and guarantee the preservation of the position of the instrument 2, 2' concerned in the absence of an action by said operator or in the case of releasing of the shaft 8 concerned, the master interface device 1 can comprise means 17, 18 for assisting with the manoeuvre and static balancing of the or of each control handle device 6, 6', preferably able to compensate for the effects of gravity during displacements of the shaft 8 and bracket 10 forming the console respectively around pivot axes PM, PE, and to maintain any current configuration of said handle 6, 6' in the absence of force applied by the operator.

According to a practical, simple and advantageous embodiment of the invention, illustrated in particular in FIGS. 3, 4 and 6 to 8, the means for assisting with the manoeuvre and static balancing are passive in type, such as simple weights.

In this case, they can comprise on the one hand a first weight 17 fixed to a section of the support part 16 extending opposite the shaft 8 relative to the pivot axis PM of the latter, and on the other hand a second weight 18 fixed to part of the second branch 11' of the bracket 10 forming the mounting console, which extends beyond the pivot axis PE of said bracket 10, in the direction of the free end of said branch 11', the securing or fixing means of said weights 17, 18 allowing an adjustment of the distances and of the relative positions of the latter relative to the aforementioned respective pivot axes PM and PE.

As shown in the aforementioned figures, said weights 17 and 18 can for example be fixed respectively onto the support part 16 and onto the bracket 10 by screws mounted in longitudinal slots arranged in said branches.

In one variant, it is also possible to make the connections 12, 13 and 14 of the articulated structure formed by each control handle device 6, 6' forms, at least partially active.

Thus, motorised means of assistance and/or variable or adaptable means of resistance (braking system) can be provided for some or each of the connections 12, 13, 14.

An arrangement of this kind (not shown specifically but well known in the state of the art) makes it possible to add movement restrictions, and therefore manipulation restrictions, as a function of the task or manoeuvre to be performed by the operator.

Figure 6:
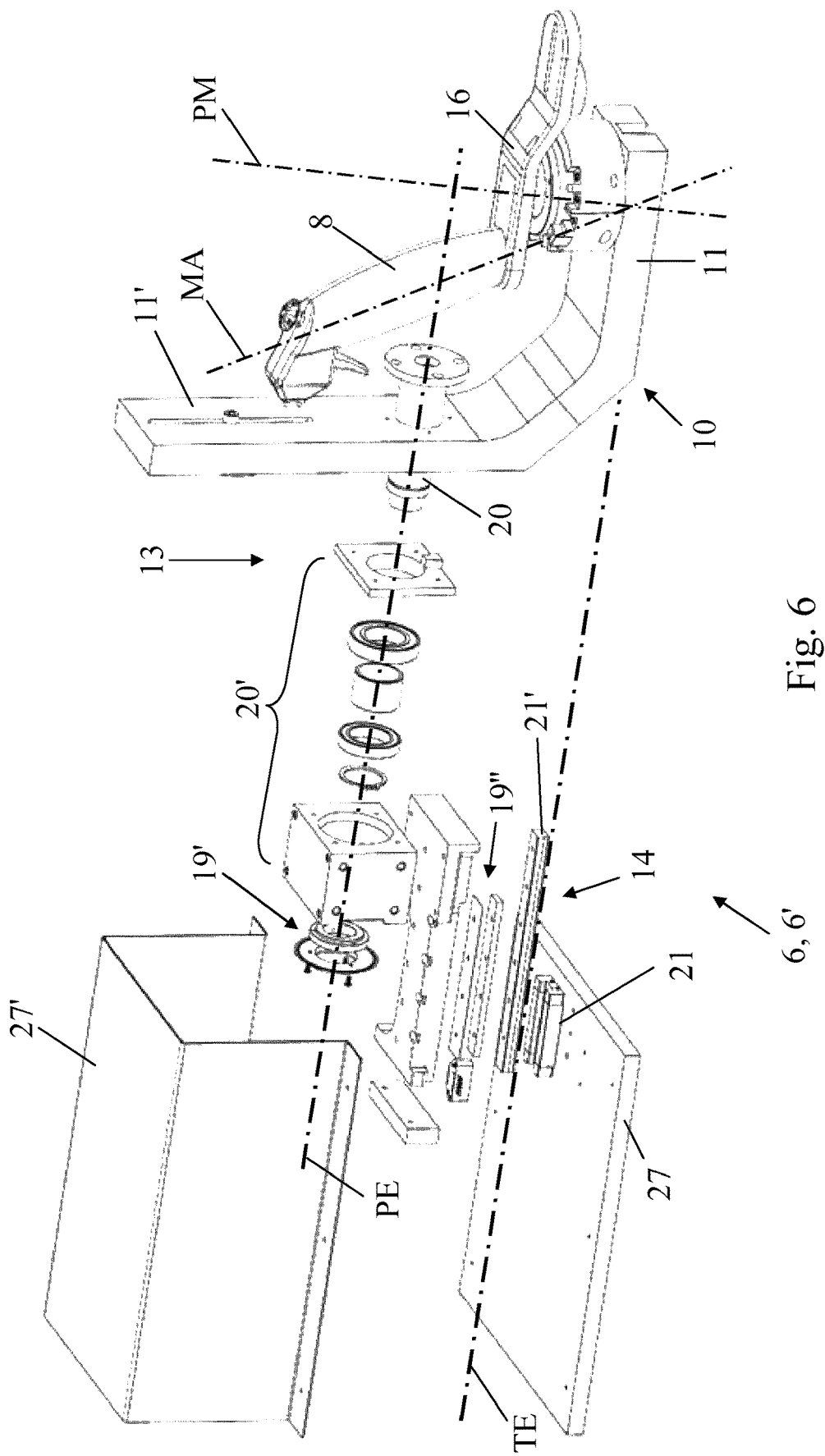
FIG. 6 is a partially exploded view of the pivot and linear guiding connection of the mounting console in the form of a bracket of the handle device of FIGS. 3 and 4.
Figure 7:
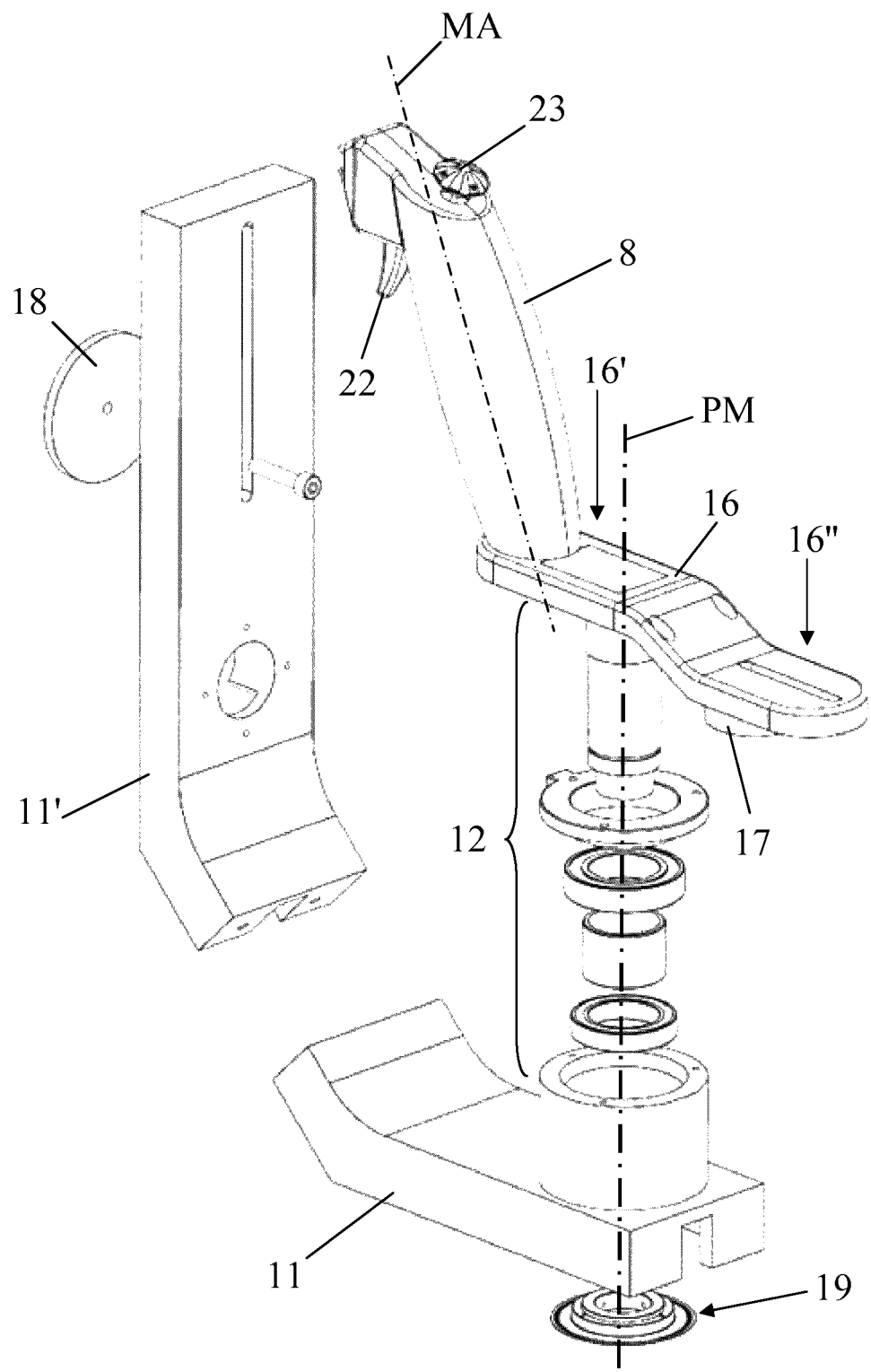
FIG. 7 is an exploded view of the pivot connection of the shaft forming part of the control handle device of FIGS. 3, 4 and 6.

FIGS. 6 and 7 illustrate, by way of example, means 19, 19', 19" for detecting rotational and translational positions, for example of the electrical-optical type, associated with each of the pivot connections 12, 13 and translation connection 14 of the or of each control handle device 6, 6' under consideration. As indicated above, the master interface device 1 can provide either position signals or displacement signals issued directly from the aforementioned means 19, 19', 19" or control signals after processing said position signals provided by said means 19, 19', 19".

Furthermore, as shown by way of example in FIG. 6, the articulated structure between the assembly bracket 10 and the fixed support structure 15 can be preferably formed by two different sub-assemblies arranged in series, namely a rotary mounting shaft 20/bearing 20' forming the pivot connection 13 and a mounting carriage 21/rail 21' forming the connection with guiding in translation 14.

The different components of the two aforementioned sub-assemblies can be mounted advantageously (at least in a position of rest) in a protective housing comprising a base plate 27 fixed onto the support 15 and a covering hood 27'.

FIG. 7 illustrates in a detailed manner a possible embodiment of the pivot connection 12 between the shaft assembly 8/support part 16 and the bracket 10, said part 16 being for example provided with a shaft mounted in rotation in a bearing forming part of the branch 11 of the bracket 10.

According to another advantageous feature of the invention and possibly as a function of the nature of the instrument 2, 2', the shaft 8 can be provided at its free end 8', with an element 22 for controlling the tool or the effector 5' of the instrument 2, 2' controlled by the control handle device 6, 6' considered, for example in the form of a trigger or the like and activated by the index finger of the operator 9 (see in particular FIGS. 3, 4, 7 and 8).

As shown in FIG. 9A, the endoscope 3 can possibly only be provided with a single instrument 2. In these conditions, the master interface device 1 only comprises a single control handle device 6 (or even two devices 6 and 6' but only one of them is active).

However, in most cases the endoscope 3 has two instruments 2 and 2' which have to be manipulated remotely by the operator 9 and consequently the master interface device 1 comprises two manual control handle devices 6 and 6', each one controlling independently a different instrument 2 or 2' in one of the working channels 3' of the same endoscope 3.

If the manipulation of the endoscope 3 is also motorised, as is the case in particular in WO-A-2013/132194 and represented in FIG. 2, the motorised degrees of freedom of said endoscope are preferably controlled via the control handle device or devices 6, 6'.

It is also possible, as shown in particular in FIGS. 3, 4, 7 and 8, that the or at least one of the two manual control handle devices 6, 6' also comprises an element 23 for controlling the bending of the end 3" of the endoscope 3, preferably in two mutually perpendicular planes (cf. FIGS. 9A and 9B), and/or for controlling the rotation and the translation of said endoscope 3 and actuating units 25, 25', preferably mounted on the same mobile structure for motorised displacement (see FIG. 2).

Preferably said element 23 is located at the free end 8' of the shaft 8 and is easily activated by the thumb of the operator 9.

Figure 4B:
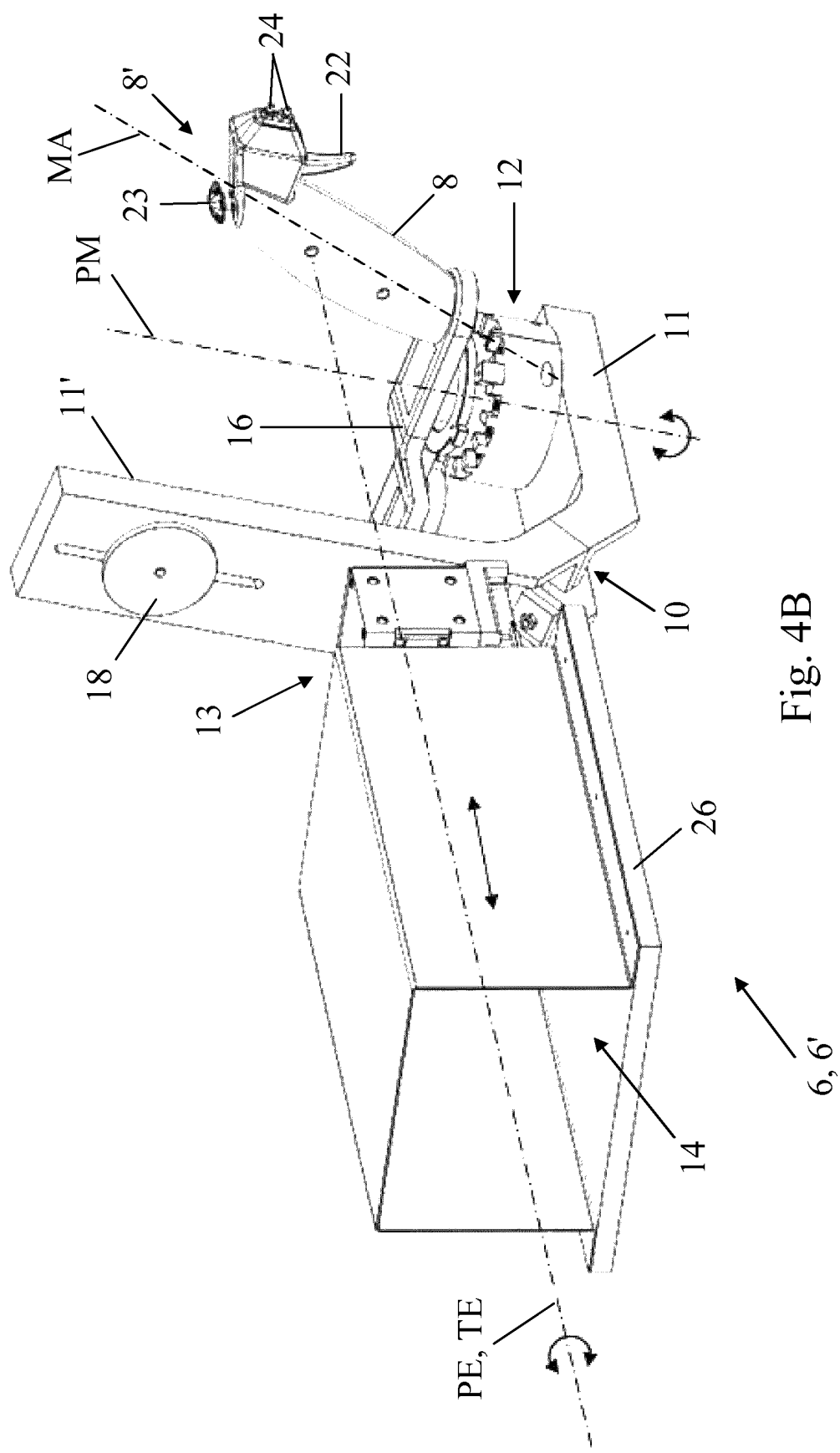
Figure 8:
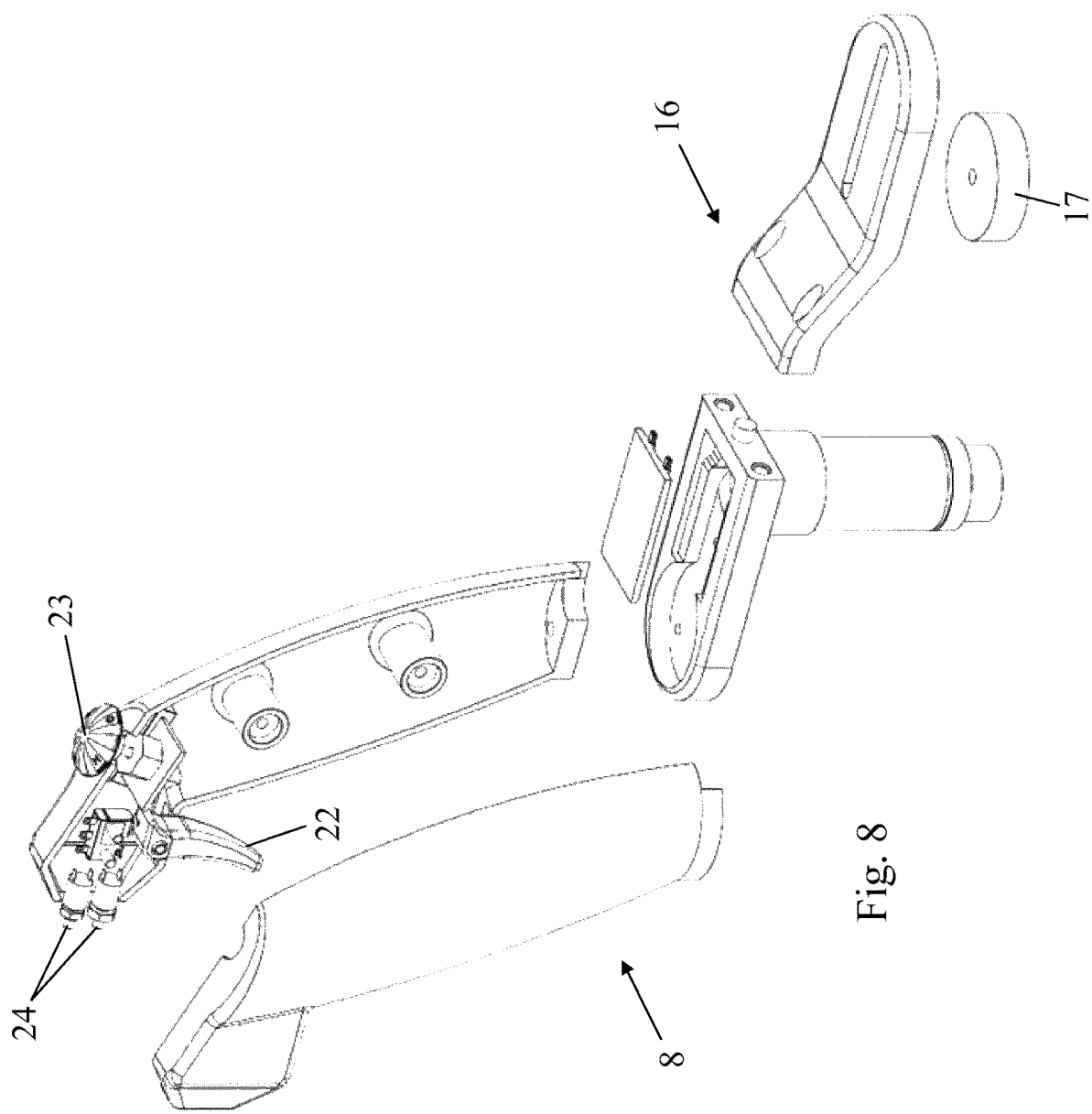
FIG. 8 is an exploded view of the shaft and its support part shown in FIG. 7.

According to another possible feature of the invention, as shown by way of example in FIGS. 3, 4B and 8, the or at least one of the two manual control handle devices 6, 6' can also be provided with one or more programmable elements 24, for example in the form of buttons or switches, located at the free end 8' of the shaft 8, and able and designed to each control a specific additional function of the instrument 2, 2', of the tool 5' or of the endoscope 3 or to inhibit a control element 22, 23 alluded to above.

The subject matter of the present invention, as shown partly in the accompanying FIGS. 1 and 2, is also a medical installation comprising an endoscopic system 4 with an endoscope 3 incorporating at least one instrument 2, 2' and a master device 1 for remotely controlling said at least one instrument, preferably also the endoscope, said or each instrument having three motorised degrees of freedom, namely the ability to perform a translational movement relative to the endoscope, an ability to rotate around itself and an ability to bend in an operational distal end 5 plane of the instrument bearing the tool or similar effector 5'.

According to the invention, the master interface device is a device 1 as described above.

Preferably, a specific modular motorised actuating unit 25, 25' is connected to each instrument 2, 2', supported by the support structure 26 of the endoscope 3.

The master interface device 1 can comprise, as already indicated above, one or two control handle devices 6, 6'.

When the latter comprises only one, the device 1 can possibly be completed by an additional control interface, of a known type, associated with the other hand of the operator which makes it possible to control other motorised functions of the endoscope and/or display functions.

Of course, the invention is not limited to the embodiment described and represented in the accompanying drawings. Modifications are still possible, particularly from the point of view of the constitution of the various elements or by substituting equivalent techniques, without departing as such from the scope of protection of the invention.

The invention claimed is:

1. A master interface device for controlling remotely at least one medical instrument for investigation or surgical intervention, the at least one medical instrument being mounted in an endoscope that forms part of an endoscopic system, in particular a flexible type in which said instrument has three motorised degrees of freedom, namely an ability to perform a translation movement relative to the endoscope, an ability to rotate around itself, and an ability to bend an operational distal end of the instrument supporting a tool or an effector,
   said master interface device being capable of and designed for delivering control signals, position, and/or displacement signals to actuating units that control the aforementioned three degrees of freedom of the instrument,
   said master interface device comprising at least one manual control handle device and a display screen for showing a video image of an intervention or investigation site provided by the endoscopic system,
   the control handle device having a sub-assembly configured to be manipulated with the same degrees of freedom as the controlled instrument, the control handle device comprising a gripping and manoeuvring shaft, a support part on which said shaft is mounted, and a mounting console supporting said shaft via said support part, said shaft is designed to be gripped with a hand of an operator, said support part having a bearing surface to support at least the hand and corresponding wrist of the operator,
   wherein said support part is connected to the mounting console by a first pivot connection with a first pivot axis which is offset from said shaft, and wherein said mounting console is connected to a support structure forming a fixed reference by a second pivot connection with an ability to pivot around a second pivot axis and by a translation connection with an ability to perform a translation movement along the second pivot axis, the axes of the first and second pivot connections being mutually intersecting,
   wherein the translation movement and the pivoting of the mounting console control respectively the translation movement and the rotation of the instrument,
   wherein displacement of the shaft relative to the mounting console, along a circular trajectory centered on the first pivot axis, controls the bending of the end of the instrument, said support part guides said displacement of the shaft according to said circular trajectory,
   wherein the first and second pivot axes are substantially perpendicular to one another.

2. The master interface device according to claim 1, wherein said support part has an elongated form, which is connected by the first pivot connection to a first branch of the mounting console said support part including a first section extending between said shaft and said first pivot connection, said first section being configured to support the hand and the wrist of the operator.

3. The master interface device according to claim 2, further comprising means for assisting with manoeuvre and static balancing of the control handle device to maintain a current configuration of said handle in the absence of force applied by the operator.

4. The master interface device according to claim 3, wherein the means for assisting with the manoeuvre and static balancing are of a passive type and comprise:
   a first weight attached to a second section of the support part, said second section extending beyond said first pivot connection opposite the shaft, and
   a second weight attached to a part of a second branch of the mounting console, said part of said second branch extends beyond the second pivot axis of said mounting console, in a direction of a free end of said second branch,
   wherein the attachment of the first weight provides for distance and position of the first weight to be adjustable relative to the first pivot axis, and the attachment of the second weight provides for distance and position of the second weight to be adjustable relative to the second pivot axis.

5. The master interface device according to claim 4, wherein the second section of the support part is configured to support a forearm of the operator.

6. The master interface device according to claim 3, wherein the means for assisting with the manoeuvre and static balancing compensates for effects of gravity during the rotation of the shaft and the mounting console respectively around the first and second pivot axes.

7. The master interface device according to claim 1, further comprising sensors that detect positions in rotation and in translation connected to each of the first pivot connection, the second pivot connection, and the translation connection,
   wherein articulation of the control handle device between the mounting console and the support structure is formed by two different sub-assemblies arranged in series, namely a rotatable mounting shaft/bearing forming the second pivot connection and a mounting carriage/rail forming the translation connection.

8. The master interface device according to claim 7, wherein the sensors are of the electrical optical type.

9. The master interface device according to claim 1, wherein a free end of the shaft comprises an element for controlling the tool or the effector of the instrument controlled by the control handle device.

10. The master interface device according to claim 9, wherein the element for controlling the tool or the effector is a trigger configured to be activated by an index finger of the operator.

11. The master interface device according to claim 1, comprising two manual control handle devices, each manual control handle device controls independently a different instrument provided in one of multiple working channels of the same endoscope.

12. The master interface device according to claim 11, wherein at least one of the two manual control handle devices comprises an element for controlling a bending of an end of the endoscope and/or for controlling rotation and translation of said endoscope, said element being located at a free end of the shaft and easily activated by a thumb of the operator.

13. The master interface device according to claim 12, wherein said element controls the bending of the end of the endoscope in two perpendicular planes.

14. The master interface device according to claim 11, wherein at least one of the two manual control handle devices comprises one or more programmable elements located at a free end of the shaft, and wherein each of the one or more programmable elements being suitable and designed for controlling a specific additional function of the instrument, the tool, or the endoscope, or inhibiting a control element.

15. The master interface device according to claim 14, wherein the one or more programmable elements comprise buttons or switches.

16. The master interface device according to claim 1, wherein the mounting console comprises a bracket.

17. A medical installation comprising:
an endoscopic system with an endoscope incorporating at least one instrument, said instrument has three motorised degrees of freedom, namely an ability to perform a translation movement relative to the endoscope, an ability to rotate around itself, and an ability to bend an operational distal end of the instrument supporting a tool or an effector, and
a master interface device for remotely controlling said at least one instrument,
said master interface device being capable of and designed for delivering control signals, position, and/or displacement signals to actuating units that control the aforementioned three degrees of freedom of the instrument,
said master interface device comprising at least one manual control handle device and a display screen for showing a video image of an intervention or investigation site provided by the endoscopic system,
the control handle device having a sub-assembly configured to be manipulated with the same degrees of freedom as the controlled instrument, the control handle device comprising a gripping and manoeuvring shaft, a support part on which said shaft is mounted, and a mounting console supporting said shaft via said support part, said shaft is designed to be gripped with a hand of an operator, said support part having a bearing surface to support at least the hand and corresponding wrist of the operator,
said support part is connected to the mounting console by a first pivot connection with a first pivot axis which is offset from said shaft, and wherein said mounting console is connected to a support structure forming a fixed reference by a second pivot connection with an ability to pivot around a second pivot axis and by a translation connection with an ability to perform a translation movement along the second pivot axis, the axes of the first and second pivot connections being mutually intersecting,
the translation movement and the pivoting of the mounting console control respectively the translation movement and the rotation of the instrument, and the displacement of the shaft relative to the mounting console, along a circular trajectory centered on the first pivot axis, controls the bending of the end of the instrument, said support part guides said displacement of the shaft according to said circular trajectory,
wherein the first and second pivot axes are substantially perpendicular to one another.

18. An installation according to claim 17, wherein each instrument is assigned to one of the actuating units.

* * * * *